United States Patent
Di Mascio et al.

(10) Patent No.: US 8,313,446 B2
(45) Date of Patent: Nov. 20, 2012

(54) INSTALLATION AND A METHOD FOR MEASURING A GEOMETRICAL CHARACTERISTIC OF AN ANATOMICAL SEGMENT OF AN INDIVIDUAL, AND A COMPUTER PROGRAM IMPLEMENTING SUCH A METHOD

(75) Inventors: Gérard Di Mascio, Bihorel (FR); Arnaud Lecerf, Sommery (FR)

(73) Assignees: Gerard Di Mascio, Bihorel (FR); Arnaud Lecerf, Sommery (FR); Eric Held, Vernon (FR)

( * ) Notice: Subject to any disclaimer, the term of this patent is extended or adjusted under 35 U.S.C. 154(b) by 912 days.

(21) Appl. No.: 11/885,235

(22) PCT Filed: Feb. 22, 2006

(86) PCT No.: PCT/FR2006/000400
§ 371 (c)(1),
(2), (4) Date: Aug. 28, 2007

(87) PCT Pub. No.: WO2006/092479
PCT Pub. Date: Sep. 8, 2006

(65) Prior Publication Data
US 2008/0200841 A1 Aug. 21, 2008

(30) Foreign Application Priority Data
Feb. 28, 2005 (FR) ...................................... 05 02021

(51) Int. Cl.
*A61B 5/103* (2006.01)
(52) U.S. Cl. ............................ 600/587; 356/603; 348/73
(58) Field of Classification Search .................. 600/587, 600/595; 356/603; 348/73
See application file for complete search history.

(56) References Cited

U.S. PATENT DOCUMENTS

| | | | | |
|---|---|---|---|---|
| 4,670,781 A * | 6/1987 | Aubert et al. | ................... | 348/77 |
| 5,016,173 A * | 5/1991 | Kenet et al. | ................... | 382/128 |
| 5,457,325 A | 10/1995 | Huberty | | |
| 6,493,095 B1 * | 12/2002 | Song et al. | ................... | 356/603 |
| 2001/0030754 A1 * | 10/2001 | Spina et al. | ................... | 356/601 |
| 2004/0032594 A1 | 2/2004 | Weber et al. | | |
| 2004/0228517 A1 * | 11/2004 | Massen | ........................ | 382/154 |

* cited by examiner

*Primary Examiner* — Max Hlindenburg
*Assistant Examiner* — Renee Danega
(74) *Attorney, Agent, or Firm* — McKenna Long & Aldridge LLP

(57) ABSTRACT

The measurement installation comprises a measurement computer system comprising: an identification system (19) that identifies a region of interest on a plane image; a pairing system (20) that determines on each plane image the two-dimensional coordinates of an anatomical point by searching for correlation between the region of interest and a corresponding zone on each other image; and a calculation unit (21) that determines the three-dimensional coordinates of the anatomical point of the individual in the measurement space on the basis of the two-dimensional coordinates and of a relationship obtained by calibration.

14 Claims, 4 Drawing Sheets

INSTALLATION AND A METHOD FOR MEASURING A GEOMETRICAL CHARACTERISTIC OF AN ANATOMICAL SEGMENT OF AN INDIVIDUAL, AND A COMPUTER PROGRAM IMPLEMENTING SUCH A METHOD

This application claims priority from PCT/FR2006/000400 filed Feb. 22, 2006, which claims priority from French Application FR 05 02021, filed Feb. 28, 2005, both of which are hereby incorporated by reference in their entirety.

FIELD OF DISCLOSURE

The present invention relates to installations and to methods for measuring a geometrical characteristic of an anatomical segment of an individual, and to computer programs implementing such methods.

BACKGROUND

It is desired to be able to determine geometrical characteristics of a human being in a given position, such as for example the respective positions of two anatomical points, the respective lengths or the relative orientation of two anatomical segments, etc.

For this purpose, it is known to use a measuring installation, such as that described in DE 4 216 458. Nevertheless, the use of matrices of sensors for placing on the body is problematic, in particular since they need to be fastened on the body and consequently lead to constraints on the posture of the individual being measured.

In addition, there is a limit on the number of measurements that can be obtained, imposed by the number and the positions of the sensor matrices used. In particular, it is not possible to measure the positions of numerous points to which it is not possible to fasten a sensor matrix.

A particular object of the present invention is to mitigate those drawbacks.

SUMMARY

To this end, the invention provides an installation for measuring at least one geometrical characteristic of an anatomical segment, said geometrical characteristic being representative of the posture of an individual placed in a measurement space, said geometrical characteristic being associated with at least one anatomical point of the individual presenting three-dimensional coordinates in the measurement space, by using a plurality of plane images of the measurement space, each taken by a detector device adapted to detect visible electromagnetic radiation coming from the measurement space, each plane image including a representation of said anatomical segment, said plane images being distinct in pairs,
said installation comprising a measurement computer system comprising:
an identification system suitable for identifying on a plane image a region of interest containing said anatomical point of the individual;
a pairing system adapted to determine on each plane image, two-dimensional coordinates of a representation of the anatomical point by searching for correlation between the region of interest and a corresponding zone on each other image;
a relationship between a geometrical measurement on each plane image and a magnitude in the measurement space, said relationship being previously established during a step of calibrating the measurement installation; and
a calculation unit adapted to determine the three-dimensional coordinates of said anatomical point of the individual in the measurement space on the basis of said two-dimensional coordinates determined by the pairing system, and of said relationship.

By means of these dispositions, it is possible to measure numerous items of geometrical information about the individual, without being limited to the locations of sensor matrices. It suffices that each anatomical segment is detectable in two plane images. When the installation is used for measuring a human being, the human being may take up a natural posture in the measurement space, thus making it possible to characterize that person's posture in pertinent manner.

In preferred embodiments of the invention, it is optionally possible also to have recourse to one and/or more of the following dispositions:

an anatomical model of the segment, said anatomical model comprising at least one model anatomical point corresponding to the anatomical point of the individual, said identification system being adapted to identify on a plane image said region of interest by using said anatomical model and processing by searching for contrast in said plane image;

a plurality of detector devices for detecting visible electromagnetic radiation coming from the measurement space, each being adapted to take a plane image of the measurement space, each plane image including a representation of said anatomical segment, said plane images being distinct in pairs;

said detector devices are each disposed to take a plane image of the measurement space at an angle of incidence, said angles of incidence, each associated with a detector device, being distinct in pairs;

the pairing system is adapted to detect a first zone on a first plane image in said region of interest, and to process at least one other plane image in order to recognize a zone similar to said first zone in each other plane image;

the anatomical segment includes at least two anatomical points of the individual, said anatomical model comprising at least one model anatomical point corresponding to each anatomical point of the individual, said calculation unit being adapted to determine said geometrical characteristic on the basis of the three-dimensional coordinates of each anatomical point in the measurement space;

said geometrical characteristic is selected from the group consisting in: a position of the anatomical segment in the measurement space; a length of the anatomical segment; an orientation of the anatomical segment relative to a straight line in the measurement space; an orientation of the anatomical segment relative to a plane in the measurement space; and an orientation of the anatomical segment relative to another anatomical segment in the measurement space;

a sighting system disposed to be visible to the individual when in the measurement space;

a system for calibrating the measurement space adapted to supply said relationship, and comprising at least one target having at least one geometrical characteristic in the measurement space that is known, said target presenting a representation on a plane image taken by each detector device in the absence of the individual in the measurement space; and the calculation unit being adapted to determine said relationship on the basis of said geometrical characteristic of the target in the measurement space, and of a geometrical property of said representation on each plane image;
- a cabin defining the measurement space, said cabin carrying said targets; and
- at least one sticker adapted to be secured releasably on the anatomical segment, said identification system being adapted to identify on at least one plane image, a representation of said sticker at a region of interest.

In another aspect, the invention provides a method of measuring at least one geometrical characteristic of an anatomical segment, said geometrical characteristic being representative of the posture of an individual placed in a measurement space, said geometrical characteristic being further associated with at least one anatomical point of the individual presenting three-dimensional coordinates in the measurement space, on the basis of a plurality of plane images of the measurement space, each taken by a detector device adapted to detect visible electromagnetic radiation coming from the measurement space, each plane image including a representation of said anatomical segment,
- said plane images being distinct in pairs,
- said method comprising the following steps:
- a) identifying on a plane image a region of interest containing said anatomical point of the individual;
- b) determining on each plane image two-dimensional coordinates of a representation of the anatomical point of the individual by searching for correlation between the region of interest and a corresponding zone on each other image; and
- c) determining the three-dimensional coordinates of said anatomical point of the individual in the measurement space on the basis of said two-dimensional coordinates determined by the pairing system, and of a relationship between a geometrical measurement on each plane image and a magnitude in the measurement space, said relationship being established previously during a step of calibrating the measurement installation.

In certain implementations, it is also possible to make provision for implementing one and/or more of the following dispositions:
- the region of interest is identified from a process of searching for contrast on said plane image, and an anatomical model of the segment, said anatomical model including at least one model anatomical point corresponding to the anatomical point of the individual;
- said anatomical model includes a plurality of model anatomical points corresponding to anatomical points of the individual, and in which steps a), b), and c) are implemented for each anatomical point of the individual;
- the method further comprises a calibration step during which a relationship is defined between a geometrical measurement on each plane image and a magnitude in the measurement space.

In another aspect, the invention provides a computer program including program code for implementing the measurement method on being executed by a programmable machine.

BRIEF DESCRIPTION OF THE DRAWINGS

Other characteristics and advantages of the invention appear from the following description of an embodiment given by way of non-limiting example and with reference to the accompanying drawings.

In the drawings.

In the various figures, the same references are used to designate elements that are identical or similar.

DETAILED DESCRIPTION OF EMBODIMENTS

Figure 1:
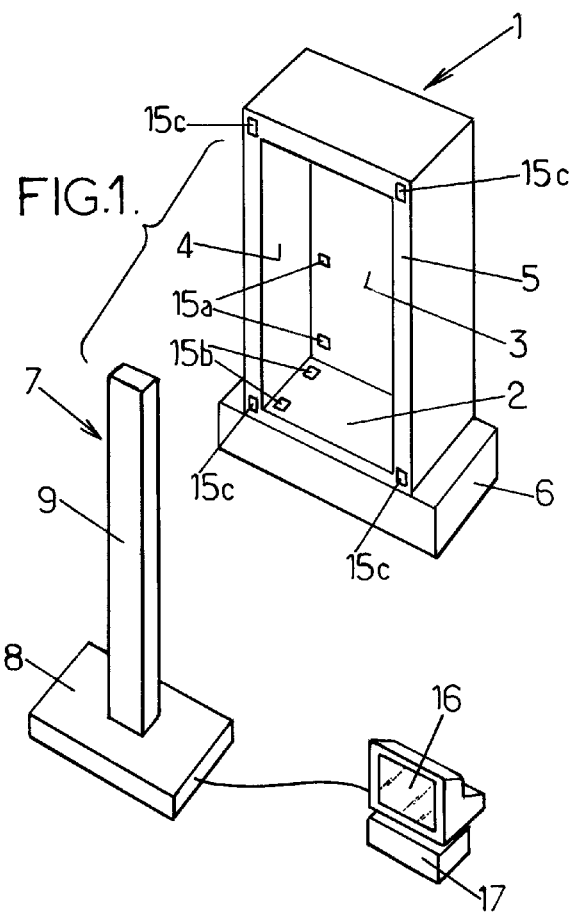
FIG. 1 is a perspective view of an embodiment of the invention.

The measurement installation shown in FIG. 1 includes a cabin 1 of sufficient size to contain a human being who is to be measured, the cabin having inside dimensions equal to 2 meters (m)×1 m×1 m, for example. The cabin 1 has a floor 1 and an inside top wall (hidden in FIG. 1) facing the floor 2, and extending substantially horizontally. It has a back wall 3 and a pair of facing internal side walls 4 (only one of which is visible in FIG. 1), e.g. of a uniform blue color and extending substantially vertically between the floor 2 and the internal top wall so as to define an internal measurement space between said walls.

The cabin 1 also includes, notably, a front face 5 that is partially open in order to enable an individual to enter into the cabin. The cabin 1 is optionally mounted on a stand 6 presenting adjustment means (not shown) enabling it to be positioned accurately horizontally.

The installation also includes a sighting and picture-taking element 7 made in the present example as a base 8 carrying a structure 9 such as a vertical upright of height substantially equal to the height of the cabin, and described below in greater detail with reference to FIG. 2.

The upright is disposed at a distance of a few meters from the cabin, having a front face 9a (not visible in FIG. 1) facing towards the cabin 1. Laterally, the sighting and picture-taking element 7 can be positioned in substantially central manner relative to the cabin 1. The position of the sighting and picture-taking element 7 relative to the cabin can be verified while the installation is in operation by a conventional alignment system, e.g. of the type comprising a laser diode in the base 8 and an auto-collimation mirror corresponding to an appropriate location of the stand 6. The relative position of the two elements can be adjusted accurately, e.g. with the help of means for adjusting the horizontal position of the base 8 and of the same type as those of the cabin 1, and by mounting the upright 9 to turn on the base 8 via a turntable 10 (FIG. 2).

Figure 2:
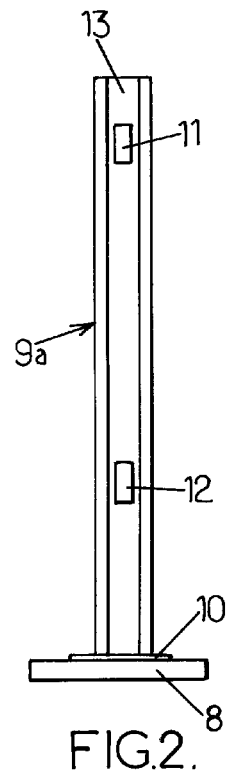
FIG. 2 is a front view in elevation of the sighting device of FIG. 1.

The front face 9a of the upright 9 is shown in FIG. 2. This front face faces the cabin 1 and includes a first detector device 11 suitable for sensing visible electromagnetic radiation coming from the cabin, such as a digital camera for taking still or moving pictures. Situated under the first detector device 11, there is a second device 12, e.g. an identical device. It should be observed that the two detector devices 11 and 12 take pictures of the cabin from two different angles of incidence. To do this, the two detector devices are disposed so that their respective focal axes together form a non-zero angle. Alternatively, the focal axes of both devices could be mutually parallel, and the devices offset relative to each other along the upright 9.

The upright 9 also carries on its front face 9a a sighting member 13, at which the individual present in the cabin 1 can look. The sighting member is implemented, for example, in the form of a dark vertical strip 13 extending vertically behind the detector devices. It may be of adjustable width.

Although the above description mentions two cameras, it would naturally be possible to use a larger number of detector devices presenting different angles of incidence in pairs.

Furthermore, the detector devices 11, 12 and the sighting member are not necessarily arranged as described above. The relative arrangement described above for the detector devices and the sighting member serves to enable plane images to be taken of the individual placed in the cabin, which images are front views when the individual is looking at (sighting) the sighting member.

The detector devices 11, 12 are connected to a computer system 17 (FIG. 1) that may be adapted to trigger picture taking, so as to store the resulting plane images obtained by the detector devices and so as to process said plane images, e.g. with the help of the Euresys Evision library.

Figure 4:
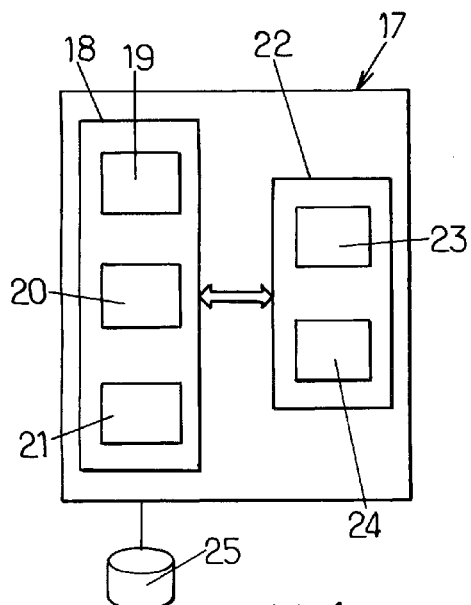
FIG. 4 is a diagram of the computer system.

The computer system 17 may be constituted as shown in FIG. 4, for example. It comprises a central unit 18 adapted to perform calculation. Purely by way of illustration, the central unit 18 comprises an identification system 19, a pairing system 20, and a calculation unit 21, as described in greater detail below, and represented herein as different software bricks. The computer system also has a memory 22 including an anatomical model 23 and a relationship 24 stored following a calibration step, serving to transform the two-dimensional coordinates of an anatomical point of the individual on each plane image into three-dimensional coordinates for said point in the measurement space, as explained in greater detail below.

The computer system 17 may also include or be remotely connected to a database 25 containing data relating to individuals and to earlier examinations of said individuals.

Figure 3A:
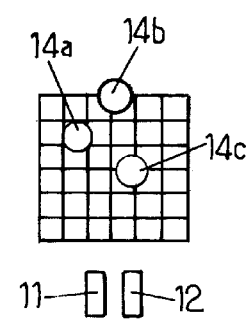
FIGS. 3a, 3b, and 3c are diagrams for explaining the principle on which the installation is calibrated.
Figure 3B:
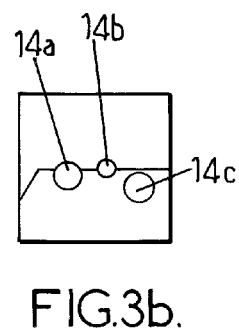
Figure 3C:
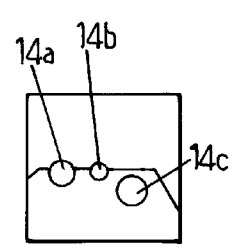

In order to obtain the relationship, it is necessary to calibrate the installation on stereoscopic principles, as explained below with reference to FIGS. 3a to 3c. During a subsequent measurement on an object, the three coordinates in the measurement space for any arbitrary point can subsequently be determined from the geometry of the system and from the positions at which said point is represented on each plane image.

In this context, it should be observed that there is no need for the anatomical point for which the three-dimensional coordinates are to be obtained to possess a visible representation on each plane image, and indeed such a representation is rare in practice. It is sufficient to be able to determine the two-dimensional coordinates that the representation of said anatomical point would have on each plane image if it were visible. These two-dimensional coordinates are obtained using the identification system 19 and the pairing system 20, as explained below.

The method used makes it possible to compare two images (the image of FIG. 3b taken by the detector device 11 of FIG. 3a, and the image of FIG. 3c taken by the detector device 12 of FIG. 3a) of the same scene (comprising three objects 14a, 14b, 14c) taken from different points of view in order to obtain information about the depth of the objects making up the scene.

This technique can be applied to a volume of isotropic dimension, but searching for pairs of corresponding points (or stereoscopic function) in the two views as needed for determining depth, puts a limit on the density of objects.

The relationship between the three-dimensional position of a point P(x) in the object field and its representation P(X) in the plane image provided by each detector device 11, 12 is formalized as follows:

$$X=F(x) \quad (1)$$

where F is known as a "mapping" function. This function is generally approximated by a polynomial of degree adapted to the phenomena that are to be corrected:

$$F(x) = a_0 + a_1 x_1 + a_2 x_2 + a_3 x_3 + a_4 x_1^2 + a_5 x_1 x_2 + a_6 x_2^2 + \\ a_7 x_1 x_3 + a_8 x_2 x_3 + a_9 x_3^2 + a_{10} x_1^3 + a_{11} x_1^2 x_2 + a_{12} x_1 x_2^2 + \\ a_{13} x_2^3 + a_{14} x_1^2 x_3 + a_{15} x_1 x_2 x_3 + a_{16} x_2^2 x_3 + a_{17} x_1 x_3^2 + a_{18} x_2 x_3^2 \quad (2)$$

For example, it is possible to select a quadratic approximation or an approximation of higher degree when the accuracy required makes that necessary.

During the calibration stage, initially a plane Z=0 is determined in which the disparity (i.e. the difference of representation between the two plane images) is zero. The positions of points are then calculated relative to the reference plane. Thereafter, it is desired to obtain values for the parameters $a_0$ to $a_9$ (in the quadratic case). To do this, during calibration, a first plane image is taken of the measurement space using the first detector device 11, and a second plane image of the measurement space is taken using the second detector device 12.

As can be seen in FIG. 1, the cabin may include calibration targets 15a, 15b, and 15c of known position and size relative to the cabin 1. Calibration targets 15a are placed on the rear face 3 of the cabin 1, e.g. nine such targets (top, bottom, and middle on both sides of the rear face 3 and on the middle vertical axis thereof). Other calibration targets 15c are placed on the front face 5 of the cabin, e.g. at its four corners. Finally, calibration targets 15b are placed on the floor 2 of the cabin 1, e.g. one in each corner.

By inverting equation (2) for a plurality of known points in the measurement space, the mapping function is obtained for the measurement space.

When the installation is put into operation, it is possible for example to proceed with calibration thereof, where such calibration depends on the position of the picture-taking and sighting element 7 relative to the cabin 1 in the dedicated room. By way of example, calibration is performed once and for all, remaining valid so long as the component elements of installation are not moved. If the cameras 11 and 12 are mounted to be movable (slidable) on the front face 9a of the picture-taking and sighting device, then calibration needs to be performed for each position of at least one camera.

It should be observed that it is possible in similar manner to obtain a mapping function solely for the floor 2, on the basis of the known coordinates and sizes of the targets 15c placed on the floor. This makes it possible to go from the coordinates of the representations on each plane image to the coordinates of the characteristic geometrical pattern in a given plane, in particular the plane of the feet, corresponding to the plane formed by the floor 2 of the cabin.

The computer system 17 is adapted to process the plane images by recognizing shapes to extract the looked-for information therefrom, as described in greater detail below. In this respect, the identification system detects a region of interest on a reference plane image, which region would contain the representation of the looked-for anatomical point supposing the point were visible in the plane image. Thereafter, the pairing system 20 determines on each plane image the two-dimensional coordinates that the anatomical point would have by searching for correlation between the region of interest defined on the reference plane image and a second image.

Figure 5:
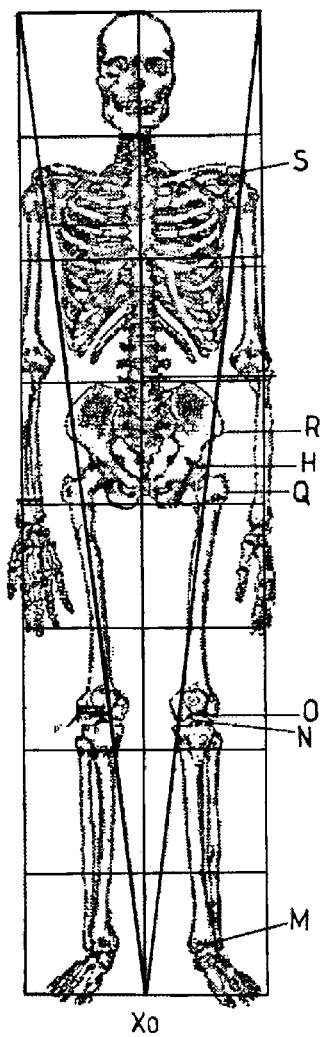
FIG. 5 is an artistic anatomical diagram for explaining the positions of certain anatomical points of the individual.

The identification system can use an anatomical model 23 stored in the memory 22 of the computer system. For example, it is possible to use an anatomical model described with reference to FIG. 5, taken from the description of anatomy for artists in the manual Struttura Umo, published by Neri Pozza editore. In that model, the body is subdivided by a grid into eight same-height segments. The eight segments correspond to the height of the subject. They are subdivided into two columns at $X_0$ so that each column comprises eight squares. The squares are numbered from the bottom up. The Z axis is the postero-anterior axis, the Y axis is vertical, and the X axis makes up the triplet of axes such that (X, Y, Z) forms a rectangular frame of reference for the cabin 1, with an origin $(X_0, Y_0, Z_0)$.

For measuring points in the bottom half, the alignment of the columns from the plane of the floor is conserved.

For measuring points in the top half of the body, the two columns (restricted to four squares) are centered on the postural eye which is assumed to be the director eye at $X'_0$ (not shown). The offset between the two verticals $X_0$ and $X'_0$ is measured.

From this grid, the two-dimensional coordinates of the anatomical points of the model are known. Finally, the calculation unit calculates the three-dimensional position of the anatomical point in the measurement space, on the basis of the coordinates obtained on each plane image.

The above-described system operates as follows:

A human being goes into the cabin in order to enable a geometrical characteristic of an anatomical segment to be measured. The geometrical characteristic may be a position, a length, or an orientation of an anatomical segment in the measurement space, or relative to another anatomical segment. This measurement involves evaluating the three-dimensional coordinates in the measurement space of at least one anatomical point such as the end of a bone, etc., which point is not necessarily visible in the plane images of the individual.

Figure 6:
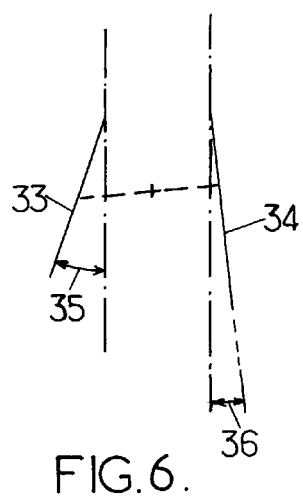
FIG. 6 is a plan view for explaining how the position of the center of the feet is obtained.

The individual can take up any position appropriate for an examination, e.g. as requested by a doctor. In particular, the individual may take up a position that is as natural as possible, staring at the sighting line 13 of the sighting and picture-taking element 7 "in the distance". Alternatively, the individual may take up the position of the anatomical model (FIG. 6). Either way, the individuals observe a narrow target in the distance. The purpose of setting position by perspective is to obtain reproducible measurements, with individuals spontaneously returning to the same locations under such conditions.

The computer system 17 causes a first plane image and a second plane image to be taken respectively by the first and second detector devices 11 and 12, e.g. simultaneously (or quasi-simultaneously).

Each plane image includes a representation of the anatomical segment. By way of example, the plane images may be pre-processed so as to be unaffected by conditions specific to the working environment (ambient lighting level, etc. . . . ). If the two images are taken by cameras 11, 12 that do not have parallel focal axes, they can be rectified so as to present a plane stereoscopic configuration. At least one of them may also be changed to match the scale of a reference image, should that be necessary. The resulting pre-processed images then represent exactly the situation shown in FIGS. 3a to 3c of two images taken by two identical cameras that are offset and that have parallel focal axes. At least one of the images is re-framed by causing a given plane to coincide in each of the plane images, e.g. the plane of the back 3 of the cabin, as identified by the targets 15a.

If two representations of a single point on the individual do not correspond exactly on the two plane images obtained after such pre-processing, that means the point does not belong to the fusion plane for the back of the cabin. It presents a depth that can be determined from the mapping functions obtained by calibration.

Nevertheless, it is necessary to identify rigorously the two representations of a single anatomical point of the individual. A priori, this is difficult since all that is available is an image of the individual's skin. By way of example, it is possible to proceed as follows: initially a grid corresponding to the grid of the anatomical model is reconstructed on a reference plane image. For this purpose, it is necessary to determine the position of the origin of the grid, which position is selected as being the mean position of the two feet in the plane of the feet, for example. By searching for contrast in a reference image, it is possible to determine the outline of each foot. by referring to the symmetry of the envelope of the foot, the longitudinal axis of each foot is determined on the reference plane image. The point of intersection between said longitudinal axis and the previously-determined envelope of the foot makes it possible to determine the ends of each foot in the reference plane image.

For each of the four points corresponding to the two ends of each of the two feet as determined in the reference image, the pairing system determines the two-dimensional coordinates of said points on each of the other plane images, in a manner that is explained in greater detail below. Thereafter, the calculation unit applies the mapping functions to the identified points on each plane image in order to obtain the three-dimensional coordinates of the corresponding anatomical points in the measurement space. As shown in FIG. 6, the middle of each foot is determined, and the origin of the grid is determined as being the midpoint between these two middles.

The size of the grid, which in the anatomical model corresponds to an individual of average height, is also modified so as to match the height of the individual being measured. Finally, the grid is deformed to match the angle of incidence from which the plane image was taken. On the basis of this information concerning the origin, concerning the height of the individual, and concerning the angle of incidence from which the reference plane image was taken, a grid is reconstructed for the individual.

The grid makes it possible to define regions of interest on each image that are the most likely to contain the looked-for anatomical point for each segment on the reference plane image.

The paragraphs below contain a description of the way in which the regions of interest for the various anatomical points under consideration are determined.

For the lower limbs, it is possible to proceed as for the foot in order to detect on the reference plane image a region of interest that is likely to contain the anatomical point that is being looked for in each anatomical segment. By searching for contrast on the reference image, the identification system identifies the outlines of the anatomical segment under study. From the determined outline, the longitudinal axis of the anatomical segment is also determined. Thereafter, a region of interest is defined corresponding to an approximate position for the anatomical point on the basis of the reconstructed grid, in the manner explained in greater detail for a particular implementation below.

The longitudinal axis of the foot 33, 34 is identified by referring to the symmetry of the envelope of the foot. The turnout-angle for each foot 35, 36 on the floor plane, and the overall V-angle are then obtained.

The advance position of one foot relative to the other in the sagittal plane along the Z axis is identified.

Figure 7:
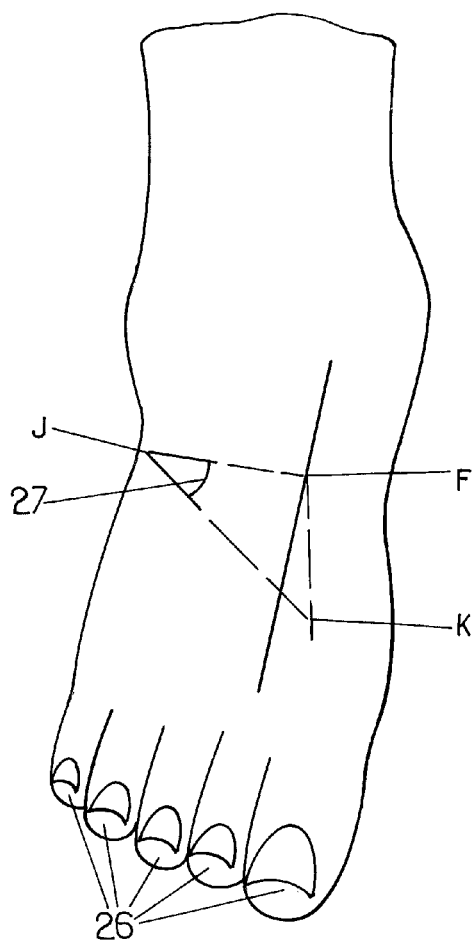
FIG. 7 is a diagram for explaining the positioning of three anatomical points on the foot.

The degree of varization (supination) or of valgization (pronation) of each foot in the frontal plane is identified as described below with reference to FIG. 7: the point F is situated facing the projection of $Y_0$ (reference vertical) on the top edge of the axis of each foot, which axis is determined by the identification system, as described above. The point J is in contact with the floor on the outer edge, perpendicularly to the axis of the foot. The point K is vertically below the point F at floor level. The degree of varization is determined manually by the angle of inclination 27 calculated between the points F, J, and K.

The axis of each phalanx 26 of each toe relative to the mean axis of the foot is identified.

To identify the ankles in the first square, the procedure is as follows: in the frontal plane, identification applies to the outer and inner malleoli which are the most proeminent anatomical elements identified as close as possible to the horizontal middle of the first square. This preeminence can be detected in the medial and lateral outlines of the ankle. The angle formed between the projection of the straight line derived from locating the lateral and medial points and the horizontal describe the bi-malleolar angle in the frontal plane. Manually pointing out the malleoli provides information concerning their rotation.

The length of each of the shins and the axis of each shin in the frontal and sagittal planes are identified as follows: length is calculated between points M and N. The point M is situated in the frontal plane at the bottom end of the shin in the middle facing the greatest width of the ankle. The point N is situated at the top of the shin at the intersection between the axes of the thigh and of the shin. The degree of frontal inclination is measured relative to the vertical. The degree of sagittal inclination is measured relative to the vertical, with the axis of the leg corresponding to the front edge of the leg being determined by the identification system. The angle formed with the thigh indicates the existence of flexion or of flexion deformity, or of extension or of recurvatum.

The positions of the thighs are identified as follows: in the frontal plane, the positions of the femurs are obtained by identifying the points O and Q. The point O corresponds to the middle of the bottom end of the femur and it is determined as being the middle of the knee, at the same Y level as the point N. The distance pp' between the point O and the outside edge of the thigh is shifted to the top of the thigh at its outermost portion and is used to determine the position of the point Q. The point Q is situated at the distance pp' from the most proeminent outside portion of the thigh and the junction between the fourth and fifth squares.

The point Q is situated in the sagittal plane, on a vertical passing through $Y_0$. The degree of frontal inclination is measured relative to the vertical in the frontal plane. The degree of sagittal inclination is measured relative to the vertical in the sagittal plane.

In the frontal plane, the distance between the inside edge of each knee and the vertical is measured. These values are compared. The angles formed between the shins and the thighs are measured. The values obtained for one side are compared with those of the other. In the sagittal plane, the angle formed between the femurs and the tibias can serve to identify the presence of flexion or of extension.

The position of the axis of the head of the femur is identified by the point H. In women, it is in the fifth square at $1/16$th of the total height of the individual relative to the vertical axis. In men, the position of the axis of the head of the femur is at $1/18$th of the total height of the individual relative to the vertical axis. Relative to the inside edge, it is at $1/4$th the length of a square. In the plane of the feet (x,z), the point H is on average situated in front of the point Q by 12°.

The positions of the antero-superior iliac spines, representative of the position of the pelvis, are identified. These positions are found relative to the point R. In the frontal plane, the point R is at the intersection between an oblique line sloping outwards and upwards from $X_0$ that terminates in the top outside corner of the 8th square and a horizontal line situated at $2/3$rds of the way from the bottom edge of the 5th square. The difference in the X positions of the top iliac spines represents the tilting and the shifting of the pelvis. The Z positioning difference of the top iliac spines represents rotation of the pelvis.

To identify abdominal points, it may be necessary to make use of marker means forming a high degree of contrast with the skin. By way of example, such marker means may be in the form of stickers stuck releasably to the skin at appropriate locations. These stickers do not hinder the individual being observed in any way. It is then possible to reconstruct the envelope of the body.

The acromio-clavicular joint is identified at point S. Point S is situated in the frontal plane in the 7th square on the oblique line starting from $X_0$ and heading to the top outside corner of the 8th square, where there is a change in contrast. In the sagittal plane, the point S lies on the axis passing through $Y_0$. These measurements give information about the positions of the shoulders.

The pupils can be identified automatically by pattern recognition in the 8th squares. Alternatively, the pupils may be pointed out manually, in particular for wearers of correcting eyeglasses. In the frontal plane, the relative positions of the pupils relative to each other can be used to evaluate the tilt of the head. The positions of the pupils in the sagittal plane are identified. The inter-pupil axis serves to situate the position of the head in the frontal plane, and makes it possible to measure the offset from the vertical passing through $X_0$. The outer auditory passages lie in the sagittal plane at point V. In the sagittal plane, the point V lies on the axis passing through $Y_0$.

Another plane image can be taken by each detector device after the individual has turned round in the cabin.

Dorsal points can be identified after identifying stickers have been placed in contact with the skin, as for abdominal stickers. The set of stickers have the characteristic of being suitable for being connected to one another automatically. One possible application is diagnosing and tracking scoliosis.

For each point F to V identified as described above, the computer system defines a region of interest, e.g. $15^2$ pixels around the identified point on the reference plane image.

Because the cameras are vertically offset, it is known that on another plane image, the representation of the same point will be on the same vertical as the identified point. In a search space in the second plane image, of height H and width L adjustable by the system, a pairing function is applied to both images. For a plurality of zones each comprising $15^2$ pixels in the search space, a correlation is calculated between the region of interest identified on the reference plane image and the current zone in the second image.

The correlation function can give directly the zone of the second plane image that corresponds to the region of interest in the first plane image.

Alternatively, it is possible to undertake a first sort only, so as to retain only a certain number of candidate zones in the second plane image, for which the correlation function gives a satisfactory result.

Thereafter, the operation is repeated for some number of zones (e.g. four) situated in a star around the region of interest defined on the first plane image. After obtaining results for all five zones, it is certain that the zone in the second plane image corresponding to the region of interest defined on the first plane image can be defined.

Provision can be made to store the positions of the representations on each of these plane images in the computer system.

From the relationship obtained during calibration of the installation, and from the two-dimensional coordinates of the anatomical points on each plane image, the exact three-dimensional position is calculated of each anatomical point.

This three-dimensional position can itself constitute the looked-for geometrical information. Alternatively, by proceeding in the same way for a second anatomical point of the segment, it is possible to obtain the three-dimensional position of a second anatomical point of the individual, and thus obtain a characteristic length or a characteristic orientation of the anatomical segment.

Alternatively, by proceeding in the same manner for a second object, it is possible to obtain geometrical information in the form of a ratio of lengths concerning two segments, or a relative orientation between two segments.

It should be observed in particular that if it is desired to obtain only angles, or relative magnitudes between segments, then it is not absolutely necessary to reduce the measurements obtained into real magnitudes, since it is possible to work using a relative scale (e.g. in terms of "cabin width" units).

It is these three-dimensional positions that are used for determining the lengths and the angles described above for the points F to V.

To identify a plurality of patterns, each identified by a sticker of given shape, it is possible to begin by processing the reference image so that the computer system applies a pattern search function to the reference plane image in order to find a given pattern in the reference plane image. For each identified pattern, the above-described processing is then applied.

The computer system can thus automatically find all of the marks placed on the body of the individual.

All of the automatic measurements can be performed manually. Any point selected manually can be localized and compared with the automatic measurements.

The vertical line passing through $X_0$ is theoretically in the middle from segment to segment. Any offset in alignment of a segment relative to the underlying segment can be quantified.

Thus, measurements obtained for the individual can be compared with the standard anatomical model as described above.

Alternatively, or subsequently, other measurements can be taken with the individual in a "natural" position, that does not correspond to a precise anatomical position defined by an anatomy manual. Such measurements can in particular be useful for providing information about certain relative angles between members, or for tracking variation in the posture of a patient over time during periodic visits.

Figure 8:
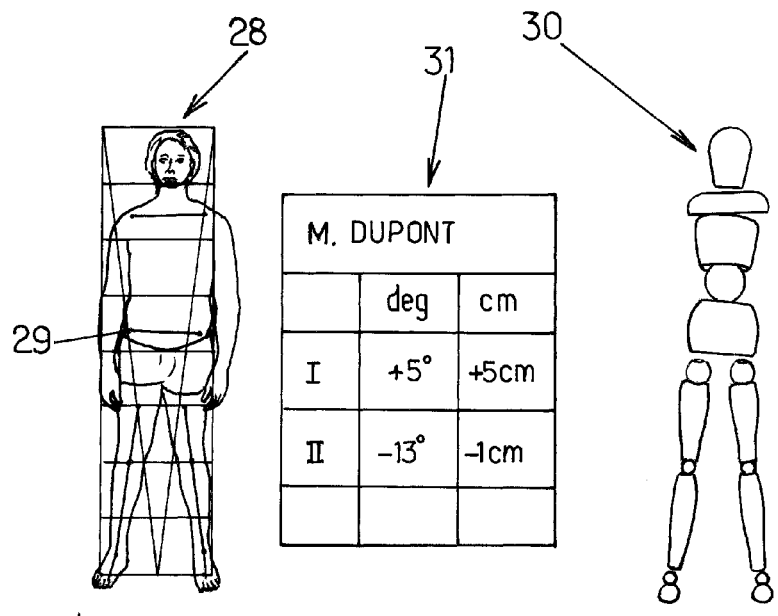
FIG. 8 is a diagrammatic view of a window in an example of supervisory software used together with the installation.

The results of the measurements can be presented on the screen 16 of the computer system 17, as shown in FIG. 8.

Figure 9:
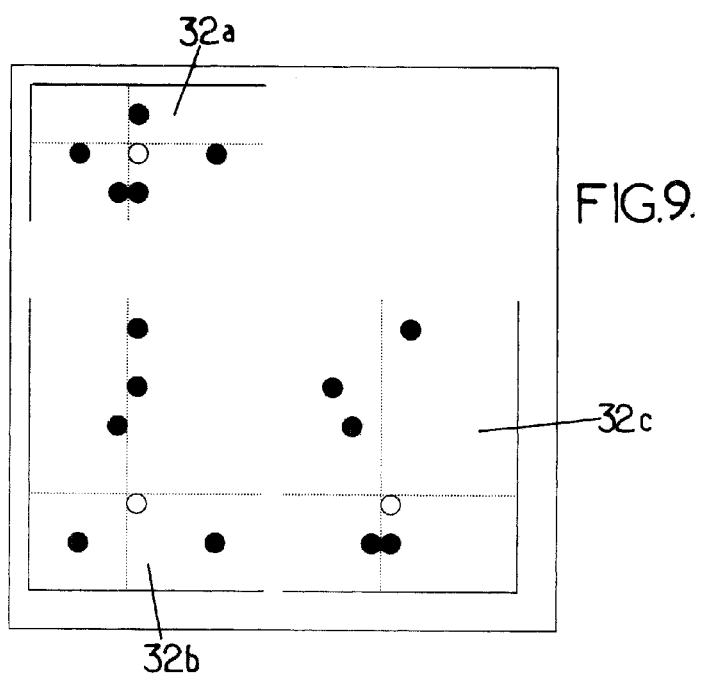
FIG. 9 is a view of a screen having three windows showing the positions of the vertebrae respectively in plan view, front view, and side view, for an individual in a natural posture.

In FIG. 8, the left-hand window 28 displays one of the plane images of the individual taken by one of the detector devices 11 or 12. The reconstructed grid is also displayed. On this image, the coordinates of the anatomical points are also obtained (see for example 29), and the corresponding three-dimensional positions reconstructed, and displayed in superposition on the photograph, or in the form of a model (right-hand window 30). A central sequence 31 can represent the numerical results of some of the measurements taken. Similarly, as shown in FIG. 9, the relative geometrical positions of vertebrae can be displayed in a plane view, in a front view, or in a side view in three distinct windows 32a, 32b, and 32c, respectively.

In order to track individuals, the data obtained can, with the agreement of the individual, be stored in confidential manner in a database 25 that is accessible from the computer system 13. The database may comprise, for each individual, static information (surname, first name, ID number, date of birth or age, sex, genetic characteristic, etc. . . . ), information that varies with each consultation (date, analog visual evaluation, measured data, information specific to the consultation, etc. . . . ), and data relative to the measurements taken (calibration parameters, configuration of the image-taking devices, three-dimensional configuration of the system, etc. . . . ).

Finally, displacements of anatomical zones can be measured by reproducing the above system using means for taking images rapidly while the individual is moving in the cabin 1.

Measurements may be taken freely in an imposed position for comparison with an anatomical model, in a rest position, in a position of maximum inclination, or in any other position deemed to be of use.

The above-described installation can also be coupled with a plate for testing stability or measuring foot pressure, etc., serving to evaluate the pressure between an individual's feet and the ground. Such a device is in the form of a platform made up of pressure sensors supporting the feet of the individual. Pressure measurement can serve to confirm and/or to add to detection of asymmetry in the posture of an individual, by correlation with measurements obtained by stereoscopic means in the meaning of the invention. Such a platform is commonly sold, in particular under the reference AM3CUBE®.

The invention claimed is:

1. An installation for measuring at least one characteristic angle of an anatomical segment, said characteristic angle being representative of the posture of an individual placed in a measurement space of the installation, said characteristic angle also being associated with at least one anatomical point of the individual presenting three-dimensional coordinates in the measurement space, by using a plurality of plane images of the measurement space, each taken by a detector device adapted to detect visible electromagnetic radiation coming from the measurement space, each plane image including a representation of said anatomical segment, said plurality of plane images being distinct in pairs, said installation having a measurement computer system comprising:

an identification system suitable for identifying on a plane image a region of interest containing said anatomical point of the individual;

a pairing system adapted to determine on each plane image, two-dimensional coordinates of a representation of the anatomical point by searching for correlation between the region of interest and a corresponding zone on each other image;

a relationship between a geometrical measurement on each plane image and a magnitude in the measurement space, said relationship being previously established during a step of calibrating the measurement installation;

a calculation unit adapted to determine the presented three-dimensional coordinates of said anatomical point of the individual in the measurement space on the basis of said two-dimensional coordinates determined by the pairing system, and of said relationship, and determine said characteristic angle of the anatomical segment; and an anatomical model of the segment, said anatomical model comprising at least one model anatomical point corresponding to the anatomical point of the individual, said identification system being adapted to identify on a plane image said region of interest by using said anatomical model and processing by searching for contrast in said plane image, said measurement installation being adapted to further compare said characteristic angle of said anatomical segment to a corresponding angle of a standard anatomical model in the same posture, in order to identify at least one angle difference between said characteristic angle of the individual and the angle of the standard anatomical model.

2. A measurement installation according to claim 1, further comprising a plurality of detector devices for detecting visible electromagnetic radiation coming from the measurement space, each being adapted to take a plane image of the measurement space, each plane image including a representation of said anatomical segment, said plane images being distinct in pairs.

3. A measurement installation according to claim 2, wherein said detector devices are each disposed to take a plane image of the measurement space at an angle of incidence, said angles of incidence, each associated with a detector device, being distinct in pairs.

4. A measurement installation according to claim 1, wherein the pairing system is adapted to detect a first zone on a first plane image in said region of interest, and to process at least one other plane image in order to recognize a zone similar to said first zone in each other plane image.

5. A measurement installation according to claim 1, wherein, the anatomical segment includes at least two anatomical points of the individual, said anatomical model comprising at least one model anatomical point corresponding to each anatomical point of the individual, said calculation unit being adapted to determine said characteristic angle on the basis of the three-dimensional coordinates of each anatomical point in the measurement space.

6. A measurement installation according to claim 1, wherein said characteristic angle is selected from the group consisting of: an orientation of the anatomical segment relative to a plane in the measurement space; and an orientation of the anatomical segment relative to another anatomical segment in the measurement space.

7. A measurement installation according to claim 1, further comprising a sighting system disposed to be visible to the individual when in the measurement space.

8. A measurement installation according to claim 1, including a system for calibrating the measurement space adapted to supply said relationship, and comprising at least one target having at least one characteristic angle in the measurement space that is known, said target presenting a representation on a plane image taken by each detector device in the absence of the individual in the measurement space; and the calculation unit being adapted to determine said relationship on the basis of said characteristic angle of the target in the measurement space, and of a geometrical property of said representation on each plane image.

9. A measurement installation according to claim 8, including a cabin defining the measurement space, said cabin carrying said targets.

10. A measurement installation according to claim 1, further comprising at least one sticker adapted to be secured releasably on the anatomical segment, said identification system being adapted to identify on at least one plane image, a representation of said sticker at a region of interest.

11. A method of measuring at least one characteristic angle of an anatomical segment, said characteristic angle being representative of the posture of an individual placed in a measurement space, said characteristic angle being further associated with at least one anatomical point of the individual presenting three-dimensional coordinates in the measurement space, on the basis of a plurality of plane images of the measurement space, each taken by a detector device adapted to detect visible electromagnetic radiation coming from the measurement space, each plane image including a representation of said anatomical segment, said plane images being distinct in pairs, said method comprising the following steps:

a) identifying on a plane image a region of interest containing said anatomical point of the individual, wherein the region of interest is identified from a process of searching for contrast on said plane image, and an anatomical model of the segment, said anatomical model including at least one model anatomical point corresponding to the anatomical point of the individual;

b) determining on each plane image two-dimensional coordinates of a representation of the anatomical point of the individual by searching for correlation between the region of interest and a corresponding zone on each other image;

c) determining the three-dimensional coordinates of said anatomical point of the individual in the measurement space on the basis of said two-dimensional coordinates determined in (b), and of a relationship between a geometrical measurement on each plane image and a magnitude in the measurement space, said relationship being established previously during a step of calibrating the measurement installation, and determining said characteristic angle of the anatomical segment; and d) comparing said characteristic angle of said anatomical segment to a corresponding angle of a standard anatomical model in the same posture in order to identify at least one angle difference between said characteristic angle of the individual and the angle of the standard anatomical model.

12. A measurement method according to claim 11, wherein said anatomical model includes a plurality of model anatomical points corresponding to anatomical points of the individual, and wherein steps a), b), and c) are implemented for each anatomical point of the individual.

13. A measurement method according to claim 11, further comprising a calibration step during which a relationship is defined between a geometrical measurement on each plane image and a magnitude in the measurement space.

14. A computer program including program code for implementing a measurement method according to any one of claims 11, 12, and 13 on being executed by a programmable machine.

* * * * *